(12) United States Patent
Leonard et al.

(10) Patent No.: US 7,029,631 B2
(45) Date of Patent: Apr. 18, 2006

(54) APPARATUS FOR IMPROVED LIGHT COLLECTION

(75) Inventors: Leslie Leonard, Portola Valley, CA (US); David King, Menlo Park, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 307 days.

(21) Appl. No.: 10/126,153

(22) Filed: Apr. 19, 2002

(65) Prior Publication Data

US 2003/0198963 A1    Oct. 23, 2003

(51) Int. Cl.
*G01N 21/64* (2006.01)

(52) U.S. Cl. .................. 422/82.08; 422/82.11

(58) Field of Classification Search .. 422/82.05–82.11; 250/458.1, 459.1; 385/12, 132, 141, 144, 385/145

See application file for complete search history.

(56) References Cited

U.S. PATENT DOCUMENTS

| | | | |
|---|---|---|---|
| 5,081,012 A | | 1/1992 | Flanagan et al. |
| 5,166,515 A | | 11/1992 | Attridge |
| 5,489,988 A | * | 2/1996 | Ackley et al. .............. 356/436 |
| 5,506,678 A | | 4/1996 | Carlsen et al. |
| 5,572,328 A | | 11/1996 | Fouckhardt et al. |
| 5,631,170 A | | 5/1997 | Attridge |
| 5,677,196 A | | 10/1997 | Herron et al. |
| 5,779,978 A | * | 7/1998 | Hartmann et al. ........ 422/82.05 |
| 5,814,565 A | | 9/1998 | Reichert et al. |
| 5,832,165 A | | 11/1998 | Reichert et al. |
| 6,224,830 B1 | * | 5/2001 | Harrison et al. .......... 422/82.11 |
| 6,316,274 B1 | * | 11/2001 | Herron et al. .............. 436/518 |
| 6,785,432 B1 | * | 8/2004 | Letant et al. ................. 385/12 |
| 2003/0113935 A1 | * | 6/2003 | Carson et al. .............. 436/165 |

OTHER PUBLICATIONS

Hecht, Jeff, "A Short History of Fiber Optics," Aug. 7, 2001, 4 pages, www.sff.net/people/Jeff.Hecht/history.html.
Ozeri, Roee et al., "Long spin relaxation times in a single-beam blue-detuned optical trap," Rapid Communications, 59:3, Mar. 1999, pp. 1750-1753.
Sarkisov, Sergey S. et al., "Untitled," Abstract Paper #2809-12, (Low-gravity factor in fabrication of thin film nonlinear optical waveguides based on photocrosslinkable polyimide, pp. 94-105) no date, 1 page.

* cited by examiner

*Primary Examiner*—Jeffrey R. Snay

(57) ABSTRACT

An apparatus for enhancing the collection of optical signals comprises a waveguide, which comprises a structure in a channel adapted for the flow of assay fluid. In one embodiment, fluorophore is coupled to a surface of the structure, where the fluorophore has a receptor for an analyte (ligand) in the assay fluid and the structure is adapted to transmit optical signals from the fluorophore to a detector that is adapted to detect optical signals from the fluorophore coupled to the waveguide.

22 Claims, 4 Drawing Sheets

APPARATUS FOR IMPROVED LIGHT COLLECTION

FIELD OF THE INVENTION

The present invention relates to enhancing the collection of optical signals. More particularly the present invention is a method for more efficiently collecting optical signals in a miniaturized system.

BACKGROUND OF THE INVENTION

Molecular assays have been successfully used to perform analytical assays. Such assays can be used for detection or recognition of antibodies, antigens, analysis of nucleic acid molecules, peptide detection, drug screening, genotyping and fingerprinting, and disease diagnosis.

An assay can contain binding molecules of several disparate species of a single type or class of molecule (e.g., DNA, or protein), each species being placed on one or more points, or features, of an assay. Analytes, such as those found in a biological sample, are washed over the entire assay in a liquid medium. Analytes bind to specific features in the assay because of specific interactions between the analytes and binding molecules. Examples of such specific interactions include, but are not limited to, antibody-antigen interactions, sequence specific nucleic acid hybridization, ligand-receptor interactions, and protein-nucleic acid interactions.

When an analyte is bound to a specific feature of an assay, a fluorescent molecule acting as an optical label can often be used to indicate the presence of the analyte. The fluorescent molecule is either attached to the analyte prior to washing over the assay, or it is attached after the analyte becomes bound to the assay. In either embodiment, the result is that fluorescent molecules are localized to those areas on the assay where binding of an analyte has occurred.

Fluorescent molecules absorb light of a specific wavelength, and then emit light at a second wavelength. Detection of light of this second wavelength from an area on an assay indicates the presence of the analyte. As the volumes in the system decrease the resulting optical signals will also decrease. In a system where the instrumentation and optics of the detector are minimized, e.g., as in a handheld instrument, the problem of decreased optical signals can be compounded.

In order to increase the accuracy of detection of the optical signals in a decreased volume, it is desired to collect the fluorescent signal in a more efficient manner. Therefore, in a situation where the biochemistry of a system results in a low signal, it is desired to have a method for focusing, enhancing or amplifying the signal. The present invention collects light more efficiently from a microfluidic domain, utilizing light enhancing techniques including waveguides, light pipes and refractive index medium enhancement.

SUMMARY OF THE INVENTION

In accordance with the invention, a method and apparatus enhancing the collection of optical signals is provided. An apparatus for enhancing the collection of optical signals comprises a waveguide structure within adapted to channel the flow of an assay fluid. In one embodiment, fluorophore is coupled to a surface of the structure, where the fluorophore has a receptor for an analyte (ligand) in the assay fluid and the structure is adapted to transmit optical signals from the fluorophore to a detector that is adapted to detect optical signals from the fluorophore coupled to the waveguide.

An apparatus for enhancing the collection of optical signals comprises a waveguide, in a conduit adapted to channel the flow of an assay fluid. The apparatus further includes a reflective coating positioned on the conduit coincident with the opening, including at least one dielectric layer. The apparatus further includes detector adapted to detect optical signals from a fluorophore coupled to an analyte in the assay fluid, where the detector is positioned coincident with the aperture.

An apparatus for enhancing the collection of optical signals, further comprises an additive to alter the refractive index of the assay fluid positioned within a conduit.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention and together with the description, serve to explain the principles of the invention.

DESCRIPTION OF THE EMBODIMENTS

Figure 1A:
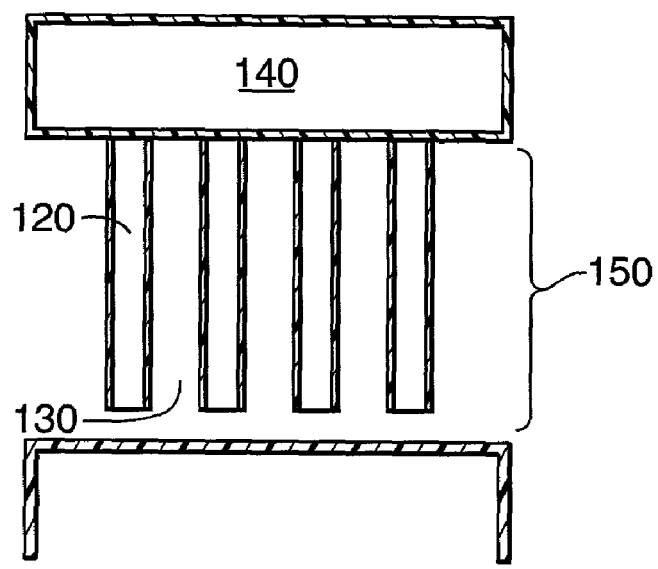
FIGS. 1A and 1B illustrate an embodiment of a waveguide finger structure.

Reference will now be made in detail to the present exemplary embodiments of the invention, examples of which are illustrated in the accompanying drawings. Wherever possible, the same reference numbers will be used throughout the drawings to refer to the same or like parts.

Certain aspects of the invention relate to collecting optical signals in a miniaturized system. The system can include an analytical assay performed in a microfluidic domain either on or near a substrate surface. The system detects fluorescence that results from interactions taking place in an analytical assay.

As embodied herein, the invention can include interactions between analytes and binding molecules. Examples of such specific interactions include antibody-antigen interactions, sequence specific nucleic acid hybridization, ligand-receptor interactions, and protein-nucleic acid interactions.

To expedite description of the invention, many of the examples herein refer to ligand-receptor interactions. The functionality of these exemplary reactions with those listed above is well known in the art of biochemistry and analytical chemistry. Therefore, these examples are for exemplary purposes only and not intended to limit the invention as claimed.

For the purposes of this specification and appended claims, unless otherwise indicated, all numbers expressing size, proportions, dimensions, quantities, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible: Any numerical value, however, inherently contains certain errors necessarily resulting from the standard deviation found in their respective testing measurements.

In certain embodiments analytical assays are performed in a system. The term "system" refers to at least one space, structure, or mechanism for fluid management. A fluid sample is introduced into the system. The fluid flows through channels, or conduits, in the system. The channels can be comprised of many various geometries. The channels can be surrounded by or be comprised of a substrate. The substrate is a layer made of a material. Within the channel, biochemical or biomolecular reactions, such as reactions involving ligand-receptor interactions, take place. The substrate can separate the channel from the detector.

Detectors can be placed in areas where the analytical assays are analyzed. Detectors suitable for the invention include CCD arrays, photodiode arrays and other array and solid-state detectors well known to those skilled in the art. Since the fluorescence is guided to the detector by the waveguide the detectors can be placed in contact with the waveguide. In certain assays the fluorescence signal is generated through a chemical interaction without the need for optical excitation. Other assays require an optical source to excite the fluorescence signal. Suitable optical sources are well known to those skilled in the art, and examples include lasers and LEDs. An optical filter, preferably a dielectric film, is placed on the detector or between the detector and the waveguide. The function of the optical filter is to separate optical excitation light emitted by either the optical source or background ambient light from the fluorescence signal.

In certain embodiments, waveguide structures can be put on the surface of a substrate in a miniaturized analytical assay system. The waveguide structure can take various forms. One form of the waveguide structure is as a waveguide finger. A waveguide finger refers to waveguide structures having a ratio of thickness to length of between 1:100 to 1:1000. In this system, a receptor/ligand capture reaction occurs on or near to the waveguide finger. Thus, light emitted from a reaction travels in the waveguide fingers. The light exiting the waveguide finger can then be directed through the substrate layer to a detector. Thus, light waves are directed to the detector.

The mode of the waveguide is not regular, thus the optical signals guided by the waveguide do not need to be the same wavelength. The mode can reflect a spectrum of values. By adjusting the diameter of the core of the waveguide in relation to its material composition, a variety of wavelengths will be able to travel along the waveguide. The mode of the material of the waveguide and the substrate should be sufficiently large so that the efficiency of the fluorescence gathering can be large. Fluorescence signal is "trapped" by the waveguide mode through evanescent coupling between the fluorescent light and the evanescent field of the waveguide mode.

The spatial extent of the evanescent field of the waveguide mode is typically of the order of an optical wavelength, which is sufficient to trap a large fraction of the emitted fluorescence—the emitting fluorophore is, typically at a distance substantially less than an optical wavelength from the surface of the waveguide. The degree of coupling between the fluorophore and the waveguide mode, and hence the amount of fluorescence trapped, depends on the effective local refractive indices of the waveguide mode and the fluorescing species. Collection efficiencies have been shown to be as large as 10% to 50% of the emitted fluorescence. The F-number approximates the ratio of the focal length to the effective diameter of an aperture. Using a large spectrum yields a higher effective F-number for fluorescence collection than a standard approach that is limited to F1, which under ideal operation can collect up to 6.25% of the emitted fluorescence. The waveguide can be fabricated from fused silica, glass, or a suitable plastic using techniques well known to those skilled in the art.

Figure 1B:
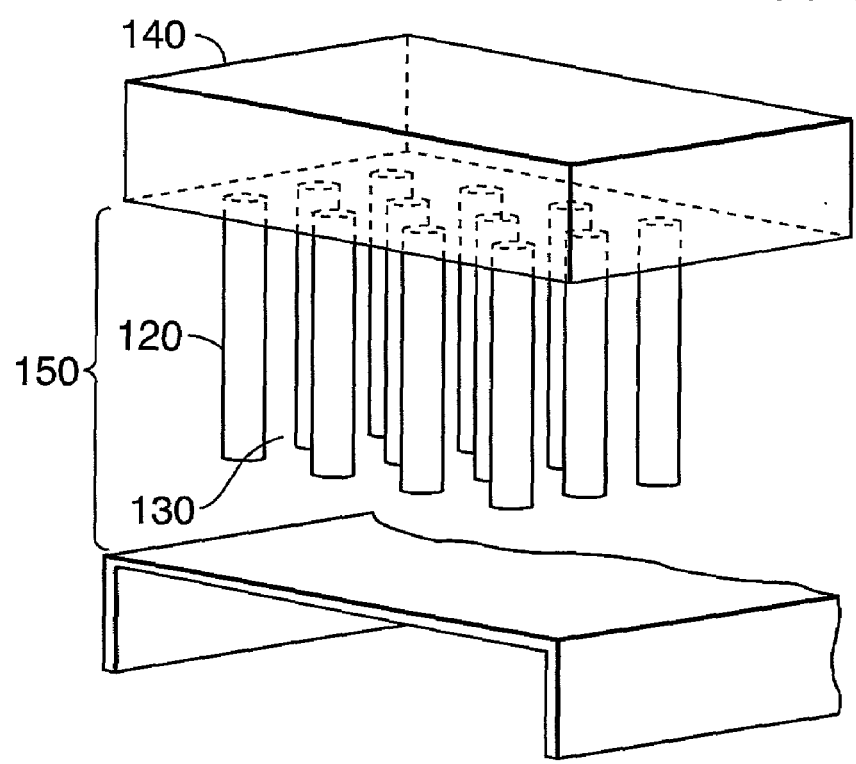

FIG. 1A illustrates a two dimensional view of waveguide fingers as a fluid flows downstream in a channel. FIG. 1B illustrates an angled three dimensional view of the channel. In the channel are waveguide fingers 120, spaces 130, substrate 140, and open channel 150. Above substrate 140 is a detector (not shown). Detectors suitable for the invention include CCD arrays, photodiode arrays and other array and solid-state detectors well known to those skilled in the art.

In FIG. 1A, the fluid in the channel flows into the page through the spaces 130. The receptors for the biomolecular interaction can be attached (attachment can be, covalent, ionic, adsorption, etc) to the surface of waveguide finger 120. When a ligand, traveling in the fluid, binds to a receptor, a portion of the resulting fluorescence is coupled into waveguide modes of waveguide fingers 120. The size of the fluorophores creating the fluorescence is many orders of magnitude smaller than the size of the waveguide fingers. The resulting fluorescence travels through waveguide fingers 120 through substrate 140 to the detector.

Waveguide fingers 120 in FIG. 1A create space 130. Space 130 facilitates the flow of fluid between waveguide fingers 120 and allows for easy introduction of the ligand to the region of the fingers. The dimensions (including depth) of waveguide fingers 120 can be optimized to enhance the spatial and frequency overlap of the fluorescence and the waveguide modes of waveguide fingers 120. The waveguide can be fabricated from fused silica, glass, or a suitable plastic using techniques well known to those skilled in the art.

Waveguide fingers 120 can be fabricated using micro-fabrication techniques. The thickness of waveguide finger 120 is optimized to create waveguide modes that optimally couple to the optical signal, while the length of the waveguide finger is determined by micro-fluidics and channel design constraints. Waveguide finger 120 thickness can be of the order of a few microns while the waveguide finger 120 length can be several hundred microns. The ratio of the thickness to length of waveguide finger 120 can range from 100:1 to 1000:1. Micro-fabrication techniques can be used to fabricate waveguide fingers 120 with such ratios. Such micro-fabrication techniques can be Deep Reactive Ion Etching (DRIE) or LIGA (an x-ray fabrication technique). Other methods known to those skilled in the art of technologies such as Micro Electro Mechanical Systems (MEMS) and nanotechnology can also be used.

Figure 2A:
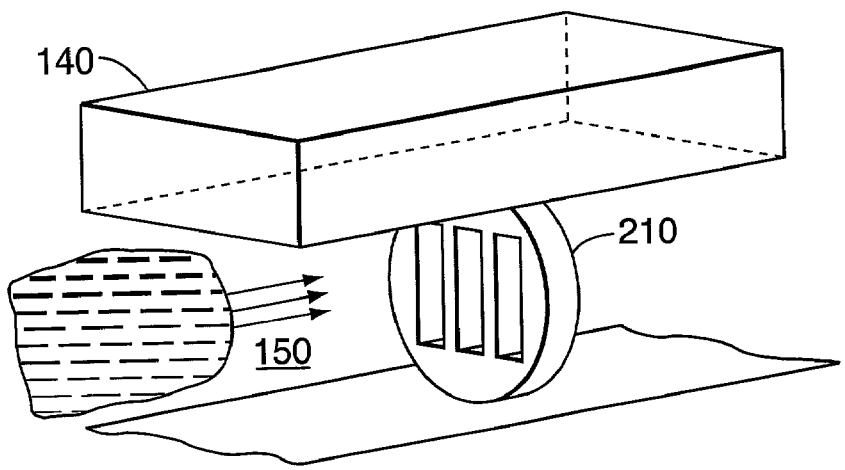
FIGS. 2A, 2B and 2C illustrate an embodiment of a waveguide filter structure.
Figure 2B:
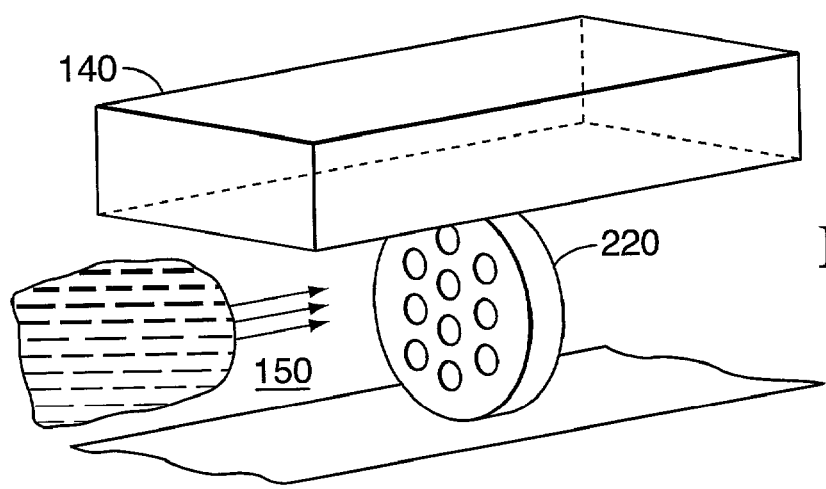
Figure 2C:
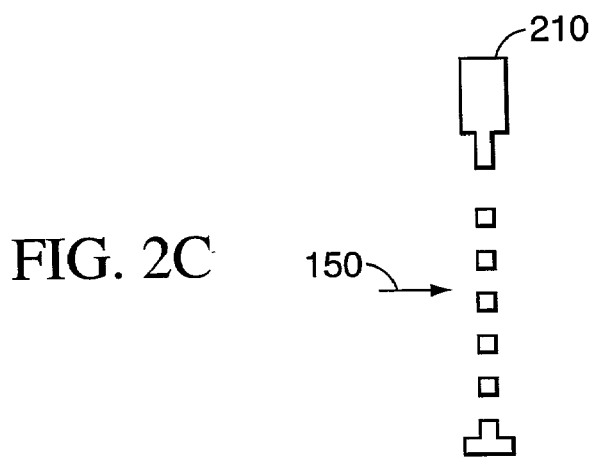

Another embodiment using the same principle is a waveguide filter as illustrated by FIGS. 2A, 2B, and 2C. FIG. 2A illustrates a type of waveguide filter. In FIG. 2A, fluid flows in open channel 150, through filter 210. Above filter 210 is a substrate layer 140, which connects open channel 150 to a detector (not shown). FIG. 2B illustrates a waveguide filter with round opening structured grate 220. Fluid flows in open channel 150 through the round opening structured grate 220. Above grate 220 is substrate layer 140, which connects open channel 150 to a detector (not shown).

FIG. 2C illustrates a cross-sectional view of filter 210 from FIG. 2A. The holes in a waveguiding filter 210 illustrated in FIG. 2C emulate the waveguide fingers 120 illustrated in FIG. 1A. Receptors are attached to the surface of the waveguide filter. The holes in the filter can be smaller than the wavelength of the light propagating in the waveguide filter. The propagation in the waveguide filter can be affected by the density and pore size of the holes in the waveguide filter. If the pore size of the hole is smaller than the wavelength of light traveling in the waveguide, then the waveguide filter material has a lower refractive index by the volume or refractive index proportion of holes to waveguide filter material. Similar techniques as those used for waveguides can be used in fabrication of the filter material and depend upon the dimensions of the microfluidic channels, the sample to be processed, and the number of molecules to be captured.

Figure 3A:
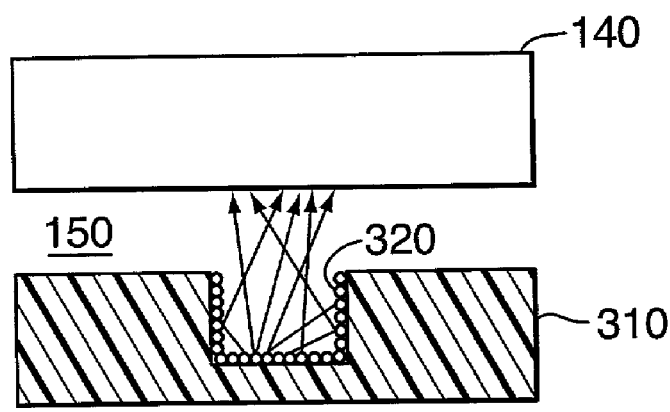
FIGS. 3A and 3B illustrate an embodiment of an etched waveguide structure.
Figure 3B:
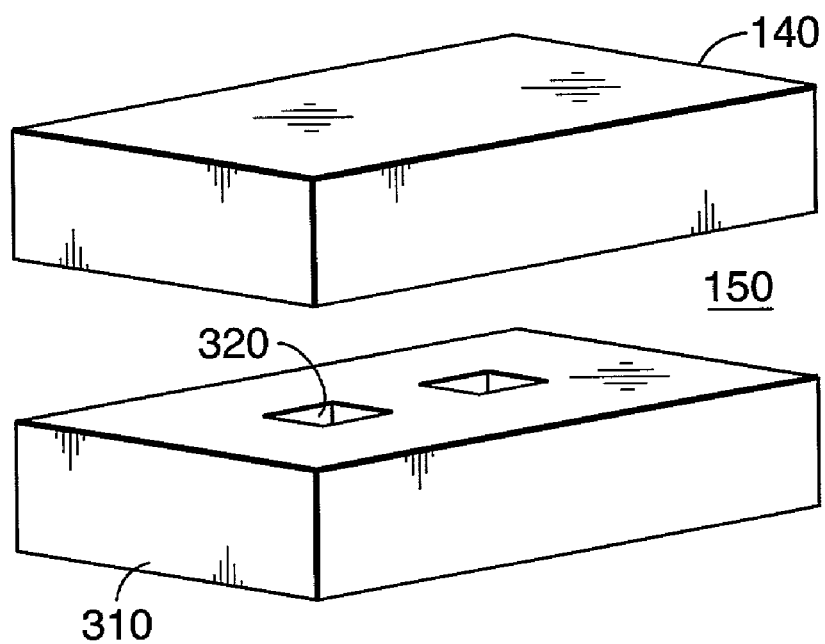

In another embodiment, illustrated by FIGS. 3A and 3B, the raised microstructure in the channel can be replaced with an inter- or sub-surface patterning 320 waveguiding structure. Patterning 320 can be created with a plasma etching technique. This technique creates three dimensionality on the order of 25–70 nanometers.

FIG. 3A illustrates sub-surface patterning 320 on substrate 310. Similar to FIG. 1A, when a ligand, traveling in the fluid in open channel 150, binds to a receptor in sub-surface patterning 320, a portion of the resulting fluorescence is amplified before traveling through substrate 140 to a detector.

In another embodiment the ligand/receptors can be contained within a three dimensional matrix of some type, e.g., an acrylamide or agarose gel, liquid chromatography media, hydrogel, sol-gel, photonic gel, or other optically active gels. This can be realized by designing the geometry of the channels such that the matrix or media is kept localized to the point of optical interrogation, e.g., by restricting the channel dimensions or angles on either side of the matrix positioned in a linear channel, or by providing a well or similar structure which would contain the matrix. This provides for three-dimensional capture of the ligand of interest and therefore, the potential for high-density of fluorophores to emit light to be captured by the waveguide. This light is then captured in a similar way as from the solid structures extending into the lumen of the channel.

In another embodiment of the present invention, the waveguide can be an aperture in a light pipe. In this case, the capture zone of the receptor/ligand is in a channel. The embodiments can include means for coating the walls of the channel with a highly reflective material so that light is collected and directed to a detector. There are two basic approaches for coating the channel with a reflecting layer, a multiplayer dielectric coating or a single highly reflective layer.

Figure 4:
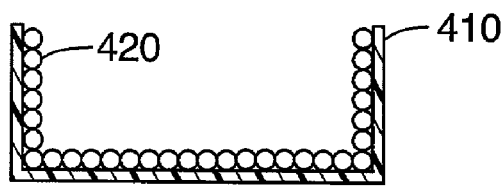
FIG. 4 illustrates an embodiment of the end view of a coated channel.

In one embodiment, illustrated by FIG. 4, a multilayer dielectric coating 420 is deposited on walls 410 of the channel region by using thin film reflectors such as, layers of $Ta_2O_5$ alternating with $SiO_2$. The thickness of each layer in this coating is approximately a quarter wavelength of the incident light. The last thin film layer, the one that will contact a biological fluid and receptor/ligand, can be one that can be functionalized or otherwise made receptive (e.g. treatment to make a surface hydrophilic, surface charge alteration, plasma etching) to biomolecular binding. In another embodiment, the $SiO_2$ layer is the final layer, because the material can itself be functionalized for binding of biological molecules by methods (covalent or otherwise) well known to one skilled in the art. Other materials could be used for the final functionalized layer. Polymers (plastics) such as polystyrene exhibit the capture and waveguiding characteristics previously described.

The receptor/ligand assay could be built as a surface capture assay on the plane of the channel nearest the detector. In this case, there can be discrete zones to specifically capture individual ligand/receptor reactions. The receptor/ligand assay could also be specifically captured within a matrix within the body of the channel (i.e. a volume reaction). In either case, the optically tagged receptor/ligand is localized to a specific site.

Figure 5A:
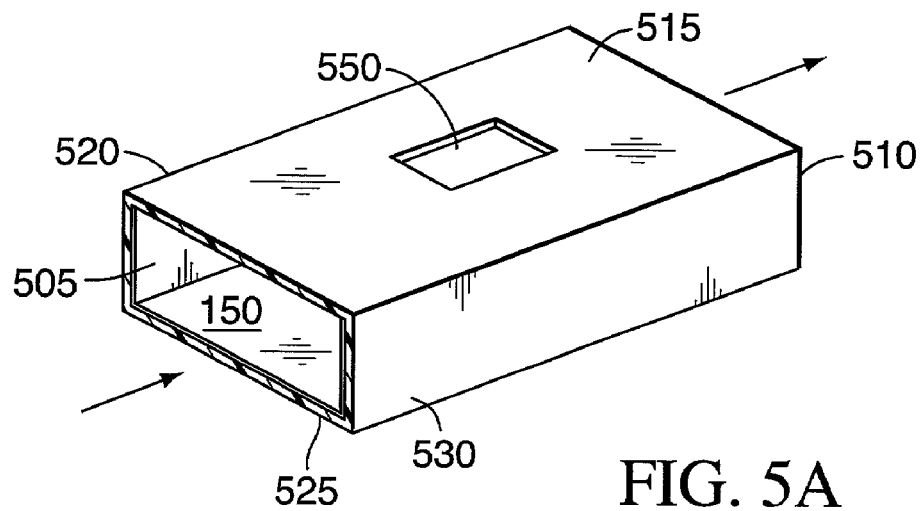
FIGS. 5A and 5B illustrate an embodiment of a light pipe.
Figure 5B:
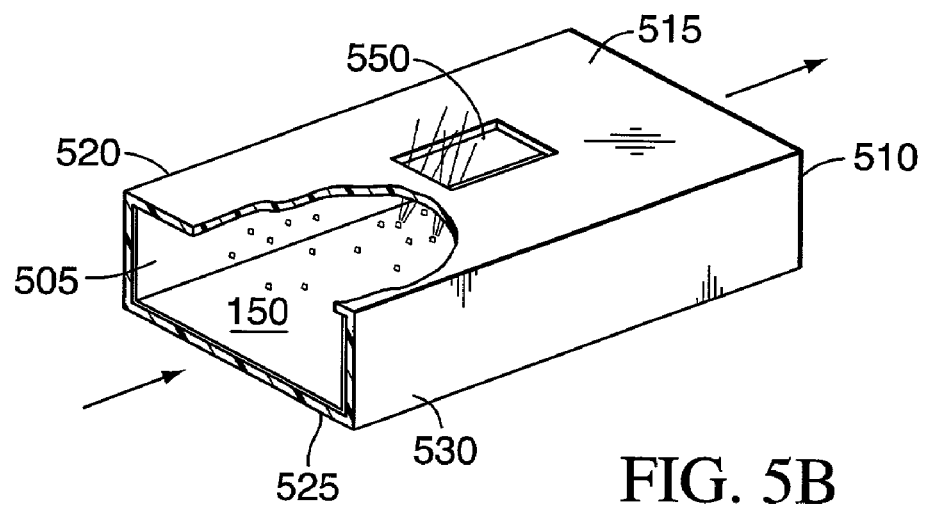

FIGS. 5A and 5B illustrate thin film layers coating on all sides of the channel with a small aperture. Light collected in the channel is directed through the aperture and onto a detector.

Fluid enters open channel 150 through opening 505 and leaves through opening 510. Aperture 550 is cut out of the channel wall 515. Channel wall 515 is the side of the channel that is closest to the detector (not shown). Channel walls 520, 525, and 530 are all coated with the multilayer dielectric coating.

In another embodiment, rather than a multilayer dielectric material, a single, highly reflective layer, e.g. gold (Au) or silver (Ag), can be patterned directly onto the polymer surface. Other dielectric materials known in the art include silicon. In the case of Ag, because it is highly chemically reactive, an additional layer of $SiO_2$ or similar material would need to be coated between the Ag and the biological material. As described above, both the Au and the $SiO_2$ can be molecularly functionalized or otherwise treated to bind biomolecules (e.g. analytes).

Another embodiment of the present invention can use the difference in refractive index (RI) of the polymer substrate and the fluid in the channel. The fluid can be biological fluids, e.g., whole blood, plasma, urine, or wash fluids that replace the biological fluid, e.g., buffers, detergent solutions, etc. In the case where the RI of the polymer is less than the RI of the fluid, the light can be waveguided within the fluid phase. An aperture, in the form of an index matching material to the fluid, is provided for light exit where desired.

Materials can be chosen that naturally differ in RI by the required amount. Substances can be added ("additives") to the fluid to artificially raise the RI (relative to the polymer) of the fluid, e.g., gold particles, perhaps compounds such as polyethylene glycols (PEGs, RI appx 1.459), particulates of other polymers, (e.g., polysulfone, RI appx 1.633) or particles with particular dyes encapsulated within. The use of gold (Au) particles can be particularly attractive because they could bring additional benefits, such as providing a substrate for a fluid phase reaction constituting a receptor/ligand assay. Such a substrate drives the reaction kinetics forward by increasing the receptor/ligand contacting in a microfluidic domain. The Au particle can also provide an environment whereby the proximity between the attached fluorophore (optical tag) and the Au surface lead to an energy transfer or similar phenomenon. This result in an enhancement or amplification of the signal.

Similar to above, for a multianalyte assay, specific capture regions can be provided. Therefore, in the case of using a particle that also serves as the substrate for the assay itself, a subsequent surface capture or capture within a 3D matrix can be accomplished.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An apparatus for enhancing the collection of optical signals that allows for flow of an assay fluid, comprising:
   one or more channel walls defining a channel, said channel adapted for flow of an assay fluid;
   a waveguide, said waveguide comprising a structure, wherein said structure includes at least one portion that protrudes into said channel adapted for assay fluid flow;
   a fluorophore coupled to a surface of said structure, said fluorophore adapted to bind with at least one analyte in said assay fluid, wherein said fluorophore generates one or more new optical signals when said fluorophore binds with said at least one analyte and wherein said structure is adapted to transmit optical signals from said fluorophore through said structure; and
   a detector adapted to detect said one or more new optical signals generated from said fluorophore, said detector coupled to said waveguide.

2. The apparatus according to claim 1, wherein:
said structure comprises at least two fingers adapted to protrude into said assay fluid flow to channel said assay fluid between said fingers.

3. The apparatus according to claim 2, wherein:
said fingers have a ratio of thickness to length of 1:100 to 1:1000.

4. The apparatus according to claim 1, wherein:
said structure comprises at least two pores adapted to channel said assay fluid flow, said pores having a diameter less than the wavelength of optical signals transmitted through said structure.

5. The apparatus according to claim 1, wherein:
said structure comprises at least two recessions etched into said waveguide, said recessions adapted to channel said assay fluid flow.

6. The apparatus according to claim 5, wherein:
said recessions are 25 to 70 nanometers wide.

7. The apparatus according to claim 1, wherein:
said structure comprises a three-dimensional matrix adapted to receive said assay fluid flow, wherein said fluorophore is arranged in a predetermined pattern within said matrix.

8. The apparatus according to claim 7, wherein:
said matrix comprises at least one material chosen from acrylamide gel, agarose gel, hydrogel, sol-gel, chromatography gel, photonic gel, and other optically active gels.

9. The apparatus according to claim 1, further including:
a reflective coating is deposited on at least one said channel wall.

10. The apparatus according to claim 9, wherein:
said reflective coating comprises two or more layers.

11. The apparatus according to claim 10, wherein:
said reflective coating comprises at least one dielectric layer.

12. The apparatus according to claim 10, wherein:
said reflective coating comprises one or more thin film reflectors.

13. The apparatus according to claim 9, comprising:
an assay fluid, wherein said assay fluid comprises at least one additive to alter a refractive index of said assay fluid.

14. The apparatus of claim 13, wherein:
said additive comprises at least one material chosen from gold, polyethylene glycol, polysulfone, and dye.

15. The apparatus according to claim 9, wherein:
said reflective coating comprises a single reflective layer.

16. The apparatus according to claim 15, wherein:
said single reflective layer comprises at least one highly reflective material chosen from gold and silver.

17. The apparatus according to claim 15, wherein:
said single reflective layer is adapted for contacting said assay fluid and comprises $SiO_2$.

18. The apparatus according to claim 15, wherein:
said single reflective layer is adapted for contacting said assay fluid and comprises a polymer.

19. The apparatus according to claim 15, wherein:
said single reflective layer comprises said fluorophore.

20. The apparatus according to claim 15 wherein:
a thickness of said single reflective layer is approximately equal to one quarter of the wavelength of incident light.

21. The apparatus according to claim 1, wherein:
said assay fluid comprises at least one additive to alter a refractive index of said assay fluid.

22. The apparatus of claim 21, wherein:
said additive comprises at least one material chosen from gold, polyethylene glycol, polysulfone, and dye.

* * * * *